United States Patent [19]

Stief

[11] Patent Number: 5,376,631
[45] Date of Patent: Dec. 27, 1994

[54] FIBRIN(OGEN) DERIVATIVES, PROCESS FOR THEIR PREPARATION AND THEIR USE

[75] Inventor: Thomas Stief, Sevilla, Spain

[73] Assignee: Behringwerke Aktiengesellschaft, Marburg/Lahn, Germany

[21] Appl. No.: 787,780

[22] Filed: Jul. 18, 1991

Related U.S. Application Data

[63] Continuation of Ser. No. 364,351, Jun. 9, 1989, abandoned.

[30] Foreign Application Priority Data

Jun. 11, 1988 [DE] Germany ............................. 3819923

[51] Int. Cl.$^5$ ........................ A61K 37/02; C07K 15/06
[52] U.S. Cl. .......................................... 514/8; 514/12; 530/382
[58] Field of Search ................ 530/382; 424/9; 514/8, 514/21; 435/13

[56] References Cited

U.S. PATENT DOCUMENTS

| | | | |
|---|---|---|---|
| 3,979,506 | 9/1976 | Smith | 424/1 |
| 4,427,646 | 1/1984 | Olexa et al. | 424/9 |
| 4,455,290 | 6/1984 | Olexa et al. | 530/382 |
| 5,057,414 | 10/1991 | Stief et al. | 435/13 |

OTHER PUBLICATIONS

Shechter et al, Biochemistry, vol. 14, No. 20 (1975) pp. 4497–4503.
Inada et al, Biochem. Biophys. Acta, 532 (1978) 161–170.
Ardaillou, et al, Biol. Abstracts vol. 72: 8464. 1981.
Mello Perisse et al, Chem. Abstracts, vol. 82: 167068h (1982).

*Primary Examiner*—Jacqueline Stone
*Attorney, Agent, or Firm*—Finnegan, Henderson, Farabow, Garrett & Dunner

[57] ABSTRACT

Oxidized derivatives of fibrin and fibrin or fibrinogen degradation products or partial sequences, process for their preparation and their use as medicaments, for diagnosis or as an affinity agent are described.

6 Claims, No Drawings

FIBRIN(OGEN) DERIVATIVES, PROCESS FOR THEIR PREPARATION AND THEIR USE

This application is a continuation of application Ser. No. 07/364,351, filed Jun. 9, 1989 now abandoned.

The invention relates to a process for the preparation of derivatives of fibrin, or fibrin or fibrinogen degradation products or partial sequences, wherein these are treated with an oxidizing agent, products prepared by this process and their use as medicaments or for diagnosis.

Human blood possesses an enzymatic system which is capable of redissolving blood clots which have formed: the fibrinolytic system.

The central enzyme in fibrinolysis, plasmin, is formed from its precursor plasminogen via activators which are liberated from endothelial cells and other cell associations. The activators can be subdivided into two types: on the one hand the plasminogen activators of the tissue type (termed t-PA) and on the other hand the plasminogen activators of the urokinase type (u-PA).

T-PA has a high affinity for fibrin, heparin, and plasmin or BrCN- degradation products of fibrinogen, and its plasminogenolytic activity is stimulated in the presence thereof.

T-PA stimulators of this type are of great interest in the therapeutic and diagnostic respect. They enable considerable dosage reductions in t-PA to be administered and promote a sensitive t-PA detection in plasma. In addition, they allow simple affinity chromatographic purifications of t-PA from biological fluids, for example cell supernatant.

Stimulators such as BrCN-degradation products of fibrinogen can, however, not be employed for therapeutic use because of their high toxicity. In vivo heparin has a low efficiency as a stimulator for t-PA.

Polymorphonuclear leukocytes and macrophages participate in physiological fibrinolysis by secretion of proteinases, inter alia urokinase, collagenase and elastase, and also of oxidation products, in this case in particular N-chloramines.

Surprisingly it has now been found that the oxidation of fibrin and fibrin or fibrinogen degradation products (FDP) caused by N-chloramines, such as chloramine T, leads to a substantial (about 5-fold to 10-fold) improvement in the t-PA-stimulating properties of these products (stimulation of unoxidized FDP=approximately 5-fold and stimulation of oxidized FDP=approximately 25-fold, compared with t-PA without stimulator). It was found that the D region of fibrinogen is the domain responsible for this effect.

The invention therefore relates to derivatives of fibrin, or fibrin or fibrinogen degradation products or partial sequences, wherein all or some of the methionine residues in the basic amino acid sequences have been converted to methionine sulfoxide residues.

The invention also relates to a process for the preparation of derivatives of fibrin, or fibrin or fibrinogen degradation products or partial sequences, which comprises treating fibrin, or fibrin or fibrinogen degradation products or partial sequences, with an oxidizing agent.

The invention also relates to a process wherein fibrinogen or fibrin is treated with an oxidizing agent and the product is degraded. Enzymatic degradation is preferred, specifically, for example, by the action of plasmin, thrombin or batroxobin on oxidized fibrinogen.

Soluble fibrin (so-called fibrin monomers) as starting material is prepared, for example, by incubating 1 mg/ml factor XIII-free fibrinogen, for example F XIII reagent, Behringwerke, in 25 mmol/l Tris, 5 mmol/l $CaCl_2$ and 2 mmol/l Gly-Pro-Arg-Pro, pH 7.8, for 10 minutes at 37° C. with 0.5 IU test thrombin and adding 5 IU hirudin/ml.

Fibrinogen degradation products can be produced in accordance with the process described by Stief et al. (Thromb. Res. 48, 603–609, 1987). A fibrinogen solution (1–10 mg/ml) in 25 mmol/l Tris and 5 mmol/l EDTA, pH 7.8, is degraded by the action of plasmin, preferably by passing the fibrinogen solution through a plasmin sepharose (2.5 mg protein/ml gel) at a flow rate of about 60 ml/h.

The oxidation of the starting materials (=fibrinogen solution or the fibrin monomers or degradation products formed) is carried out at pH 7–9.5, preferably in a buffer, in particular Tris buffer, if appropriate with the addition of 0.01–0.2 and preferably 0.1% (w/v) detergent, such as $^R$Triton X 100, and, if appropriate, with the addition of mannitol, preferably 5–20mmol/l, to improve the solubility. The oxidizing agent used is preferably a chloramine, such as chloramine T, specifically in a concentration of 1–20 mmol/l, preferably 5–10 mmol/l. The oxidation can be terminated by adding an excess of reducing agent, such as ascorbic acid, acetylcysteine or acetylmethionine. The oxidation can be carried out at 4°–45° C., preferably 20°–40° C., and proceeds within seconds (less than 5 min).

The end products are characterized by amino acid analysis. After protein oxidation, methionine is detected only in traces whereas methionine sulfoxide is detected in amounts which correspond to the methionine content occurring in the protein. The plasmin-degraded and oxidized derivatives also possess a better solubility in distilled water than the unoxidized derivatives.

Synthetic methionine-containing peptides containing sequences from the D-region of fibrinogen are also suitable as starting material for the process according to the invention. Oxidized FDP bind t-PA and sc-uPA (single chain form urokinase) with a higher affinity than unoxidized FDP, as shown in tests with FDP covalently bonded to $^R$Sepharose 4B. For this reason oxidized fibrin and fibrinogen derivatives are particularly suitable for purifying t-PA or sc-uPA (for example from cell supernatants) by affinity chromatography.

Suitable oxidizing agents are, in particular, methionine-specific oxidants, which preferably convert methionine to methionine sulfoxide in an alkali medium, preferably chloramines (for example chloramine T or chloramine B), or salts of hypochlorous acid (for example NaOCl). According to Savige and Fontana (Methods in Enzymology 47: 453–459, 1977), dye (for example methylene blue)-mediated photooxidation and also bromosuccinimide; N-chlorosuccinimide; 2,4,5-tribromo-4-methylcyclohexadienone; BNPS-skatole (2-(2-nitrophenylsulfonyl)-3-methyl-3-bromoindolamine); chloramine T; t-butyl hypochlorite; trichloromethanesulfonyl chloride and also 1-chlorobenzotriazole, iodobenzene dichloride in aqueous pyridine, pyridine bromide complexes, quinolines and, in particular, 1,4-diazobicyclo(2.2.2)octanes in aqueous acetic acid are suitable for the conversion of methionine to methionine sulfoxide.

The oxidation, preferably at pH 8–9, is improved by the addition of 0.05–0.1% detergent, such as $^R$Triton X 100.

Oxidized FDP likewise bind to fibrin with a considerably higher affinity than non-oxidized FDP, as can be shown in tests with clotted plasma. For this reason they are particularly suitable for directing substances valuable for thrombus diagnosis and therapy to a clot in vivo.

According to the state of the art, thrombi are detected in vivo using radioactively labeled fibrinogen (Mahn, I., and Müller-Berghaus, G., Haemostatis, 4: 40:50, 1975). Since oxidized FDP possess a considerably higher affinity for the thrombus than fibrinogen, the use of radio-actively labeled oxidized FDP, preferably FDP-D, is more advantageous since 1. the clinical findings are available within a shorter time (less than 1 h) after administration of the diagnostic agent and 2. the total organism is subjected to lower radioactive doses since less labeled protein is required because of the high affinity.

On the other hand, according to the state of the art, plasminogen activators (PA) are transported to fibrin clots by using PA covalently bonded to fibrin antibodies or chimeras of PA and fibrin antibodies produced by gene technology.

Disadvantages of these methods lie in the induction of antibodies against the protein foreign to the body. The side effects associated herewith (for example immune complex diseases) can be avoided by the use of human oxidized FDP.

HOCl- and chloramine-producing enzymes, such as myeloper-oxidase, glucose oxidase and xanthine oxidase can also be transported to a thrombus by means of oxidized FDP if they are in a covalently bonded state with oxidized FDP. The enzyme reaction can be started by infusion of suitable non-toxic substrates (for example glucose, xanthine, hypoxanthine). Oxidation of fibrin polymers in vivo lowers the requirement for endogenous and, if necessary, foreign t-PA to dissolve a thrombus, as a result of which, only small amounts of t-PA have to be administered for a successful lysis. The associated oxidative inactivation of the fibrinolysis inhibitor alpha-2-antiplasmin bonded in the thrombus intensifies the profibrinolytic effects.

In addition, intravenous administration of oxidized FDP gives rise to an intensified generalized stimulation of t-PA and sc-uPA, as a result of which the dose of this PA can be reduced or its use can be dispensed with entirely.

Furthermore, oxidized fibrin(ogen) derivatives are suitable for a sensitive and specific detection of plasminogen activators which can be stimulated, such as t-PA, in in vitro test systems in plasma or other biological fluids. For this purpose, for example, 50–200 $\mu$g of oxidized fibrinogen degradation products/ml reaction batch are used in a chromogenic detection method for t-PA together with 3 CTA-U plasminogen and 0.3 $\mu$M of a chromogenic plasmin substrate.

EXAMPLE 1

Preparation of the oxidized fibrinogen degradation products a) Plasmin degradation products 250 mg of test fibrinogen (Behringwerke) dissolved in 50 ml of distilled water with 5 mmol/l EDTA were passed through 25 ml plasmin- $^R$Sepharose 4B (2.5 mg plasmin/ml gel) at a flow rate of 60 ml/h at room temperature (RT). The effluent (Eff.) was adjusted to pH 8.5, 12.5 ml of 100 mmol/l chloramine T were added and the mixture was incubated for 15 minutes at 37° C.

The oxidation batch was then dialyzed (48 h, 4° C.) against the 200-fold volume of 50 mmol/l Tris, pH 8.5.

Alternatively, the oxidized degradation products could be obtained by an oxidation taking place prior to passage through the plasmin-sepharose and subsequent plasmin proteolysis.

b) Thrombin degradation products

Thrombin degradation products, according to the invention, of oxidized fibrinogen are obtained by first oxidizing 1 mg/ml fibrinogen with chloramine T at a concentration of 2.5 mmol/l and then incubating with 0.5 IU test thrombin (Behringwerke) for 10 minutes at 37° C. and pH 7.8 and adding 5 IU hirudin/ml.

EXAMPLE 2

Stimulation of the plasminogenolytic activity of t-PA by FDP as a function of the oxidizing agent concentration—detection of t-PA by oxidized FDP a) 100 $\mu$g of FDP-BrCN (FDP prepared via BrCN degradation) and, respectively, 100 $\mu$g of FDP-EDTA (FDP prepared via plasmin degradation in the presence of EDTA) in 100 $\mu$l of 50 mmol/l Tris, 100 mmol/l NaCl, 0.01% $^R$Triton X 100, pH 8.5, and Tris buffer without FDP were incubated with 50 $\mu$l of chloramine T of various concentrations (0–20 mmol/l) in distilled water for 10 min at 37° C. After adding 100 $\mu$l of 3mmol/l HD-Nva-CHA-Lys-pNA in distilled water, 200 $\mu$l of 1.3 $\mu$mol/l Glu-plasminogen in 100 mmol/l Tris, 100 mmol/l NaCl, 1% Haemaccel and 0.1% $^R$Triton X 100, pH 8.4 (TNHT buffer), and 10 IU two-chain t-PA in 200 $\mu$l of TNHT buffer, a further incubation for 12 min at 37° C. took place. The conversion of the substrate was terminated by adding 500 $\mu$l of 3.4 mol/l acetic acid and the resulting change in absorption at 405 nm was detected.

b) In a variation, the oxidation of the FDP by addition of 50 $\mu$l of 10 mmol/l chloramine T was terminated after 10 min (37° C.) pre-incubation by adding 50 $\mu$l of 5 mmol/l dithiotreitol and the plasminogen activation was then carried out.

Result from Example 2a, b:

TABLE 1

| Chloramine T (concentration in 50 $\mu$l addition) | Fibrinogen degradation products | | |
|---|---|---|---|
| | BrCN-degraded | with EDTA through plasmin-seph. | without FDP |
| | Plasmin activity ($A_{405\ nm}$; mE) | | |
| 0 mmol/l | 898 | 1053 | 122 |
| 1 mmol/l | 1007 | 947 | 132 |
| 2.5 mmol/l | 1067 | 1310 | 134 |
| 5 mmol/l | 914 | 1936 | 135 |
| 7.5 mmol/l | 728 | 2218 | 136 |
| 10 mmol/l | 517 | 2315 | 132 |
| 15 mmol/l | 220 | 2091 | 118 |
| 20 mmol/l | 138 | 1900 | 98 |
| 10 mmol/l / 5 mmol/l DTT | 806 | 2356 | 129 |

Increasing concentrations of chloramine T lead to an increased capacity for t-PA stimulation. FDP-EDTA and FDP-BrCN show an improvement in their stimulation of t-PA which is only minimal (10%) and is only found at low chloramine T concentration. Higher chloramine T concentrations lead to an impairment in the t-PA stimulation.

EXAMPLE 3

Stimulation of the plasminogenolytic activity of t-PA by different FDP S- t-PA detection by FDP 100 μg each of FDP-BrCN, FDP-EDTA, fibrinogen and FDP-EDTA obtained by passing oxidized fibrinogen (see Example 1) through a plasmin-$^R$Sepharose were examined in accordance with the test conditions listed in Example 2a) with the addition of 50 μl of 20 mmol/l chloralnine T and distilled water to check their stimulating power towards two-chain t-PA. The oxidation was terminated after 10 min (37° C.) by adding 100 μl of 6.25 mmol/l dithiotreitol and the substrate conversion was terminated after 9 min (37° C.) by adding 500 μl of 3.4 mol/l acetic acid.

See Table 2 for the result.

In the case of FDP-EDTA, oxidation in the test leads to a pronounced rise in the t-PA-stimulation power. Before oxidation in the assay, FDP-BrCN and FDP-EDTA from preoxidized fibrinogen already possess more than 10 times the stimulation power as compared with the buffer control. The oxidation of fibrinogen also increases its stimulation potential.

TABLE 2

| Stimulant | Distilled water | 50 μl of 20 mmol/l chloramine T |
|---|---|---|
| | Plasmin activity ($A_{405\,nm}$; mE) | |
| FDP-BrCN | 443 | 614 |
| FDP-EDTA | 276 | 1172 |
| FDP-EDTA (from preoxidized fibrinogen) | 485 | 962 |
| Fibrinogen | 117 | 156 |
| Buffer control | 30 | 27 |

EXAMPLE 4

Affinity chromatographic purification of t-PA and sc-uPA by immobilized oxidized fibrin or fibrinogen degradation products and derivatives 1 ml aliquots of single chain (sc)-t-PA, sc-uPA and two-chain (tc)-uPA (1 μg/ml) in TNHT buffer were incubated for 45 min at room temperature with, in each case, 0–300 μl of a 50% strength FDP-EDTA solution or oxidized FDP-EDTA-$^R$Sepharose 4B (2 mg protein/ml gel) with a gentle shaking. After centrifugation, the supernatants were removed and tested for their plasminogenolytic activity. The residual activity was expressed in percent of the initial activity. 100 times the amount of TNHT buffer was added to the $^R$Sepharose 4B remaining in the sediment and the whole was mixed thoroughly and centrifuged again. The supernatant was decanted off and 1 ml of eluent was added. 2M KSCN and 1% sodium dodecyl sulfate were used for this purpose. 10 minutes incubation (RT) with shaking were followed by centrifugation and dialysis (48 h, 4° C.) against 200 times the volume of TNHT buffer. The samples were then tested for their plasminogenolytic activity.

Plasminogenolytic activities were determined by incubating 50 μl of sample (supernatant liquor) with 100 μg of FDP-BrCN, 278 pM of Glu-plasminogen and 0.3 μmol of HD-Nva-CHA-Lys-pNA in a volume of 600 μl for 5 min at 37° C. The conversion of the substrate was terminated by adding 500 μl of 3.4 mol/l acetic acid and the resulting extinction at 405 nm was determined.

Result:

Immobilized, oxidized FDP-EDTA show a considerably higher affinity for t-PA than unoxidized FDP. In contrast to u-PA, sc-uPA shows an affinity for bonding to oxidized FDP. The elution of the bound PA molecules can be effected by 2 mol/l KSCN or 1% SDS.

TABLE 3

| Oxidized (non-oxidized) 50% strength FDP-sepharose (μl) added | Residual activity in the supernatant liquor | | | | | |
|---|---|---|---|---|---|---|
| | sc-t-PA | | sc-u-PA | | tc-u-PA | |
| | (%) of the initial activity | | | | | |
| 0 | 100 | (100) | 100 | (100) | 100 | (100) |
| 20 | 97 | (100) | 100 | (100) | 100 | (98) |
| 50 | 85 | (100) | 94 | (100) | 100 | (100) |
| 100 | 55 | (87) | 91 | (97) | 97 | (100) |
| 200 | 47 | (81) | 78 | (92) | 96 | (99) |
| 300 | 31 | (47) | 55 | (90) | 90 | (96) |

EXAMPLE 5

Separation of the oxidized and non-oxidized fibrinogen degradation products through DEAE-Sephacel and subsequent polyacrylamide gel electrophoresis (PAGE) and assay of stimulation by the individual fragments.

The effluent from the plasmin-sepharose, as indicated in Example 1, was re-dialyzed against 200 times the volume of 10 mmol/l sodium phosphate buffer, pH 8.6. The dialysate was then applied to 100 ml of the DEAE-Sephacel pre-equilibrated with three times the column volume of 10 mmol/l sodium phosphate. Elution (10 mmol/l sodium phosphate, pH 8.6, and 300 mmol/h potassium hydrogen phosphate, pH 4.3, 100 ml in each case) was then carried out at a flow rate of 60 ml/h at room temperature by means of an increasing ionic strength and decreasing pH gradient. 3 ml fractions were collected.

Effluent (before applying of the gradient) and individual peaks were examined with respect to optical density at 280 nm and also in sodium dodecylsulfate PAGE (see Tables 4 and 5 for results). Fibrinogen degradation products by plasmin degradation possess the following approximate molecular weights(KDa): fibrinogen 340, X 300, Y 150, D 90, 87, 85, E 60.

TABLE 4

Non-oxidized starting material

| | Fraction No. | $OD_{280\,nm}$ | Main bands (subsidiary bands) in SDS gel, unreduced (KDa) |
|---|---|---|---|
| Effluent | 14–29 | 0.7 | 90 |
| Peak 1 | 47–50 | 4.4 | 90, 85 |
| Peak 2 | 51–54 | 5.6 | 90 (300, 60, 150) |
| Peak 3 | 55–58 | 0.46 | 90, 60 (300, 150) |
| Peak 5 | 83–89 | 0.3 | 60, 300 (150) |
| Peak 6 | 90–98 | 0.32 | 60 (300) |
| Peak 7 | 109–113 | 0.1 | (90, 300) |

Peak 1 corresponds to fibrinogen fragment D.

TABLE 5

Oxidized starting material

| | Fraction No. | $OD_{280\,nm}$ | Main bands (subsidiary bands) in SDS gel, unreduced (KDa) |
|---|---|---|---|
| Effluent | 12–30 | 0.34 | (90, 60, 150, 300) |
| Peak 1 | 53–55 | 0.4 | 90 |
| Peak 2 | 56–60 | 0.98 | 85 |
| Peak 3 | 61–67 | 2.2 | 90 |
| Peak 4 | 85–98 | 0.72 | 60, 300, 150 |

TABLE 5-continued

Oxidized starting material

| Fraction No. | OD$_{280\,nm}$ | Main bands (subsidiary bands) in SDS gel, unreduced (KDa) |
|---|---|---|
| Peak 5  109–120 | 0.08 | 300 (90) |

Peaks 1–3 correspond to fibrinogen fragment D.

100 μl of the individual fractions from the DEAE separation of unoxidized FDP (EDTA) were examined in accordance with Example 2 for their t-PA-stimulating activity in the unoxidized and oxidized state. See Table 6 for results.

TABLE 6

| Addition of 50 μl | a) distilled water | b) 20 mmol/l chloramine T |
|---|---|---|
| | Plasmin activity A$_{405\,nm}$/9 min (mE) | |
| Effluent (main band in SDS gel) | 184 | 703 |
| Peak 1 (FDP-D) | 320 | 1890 |
| Peak 2 (FDP-D) | 451 | 1728 |
| Peak 3 (FDP-D, E) | 583 | 1145 |
| Peak 5 (E, X) | 266 | 223 |
| Peak 6 (E) | 197 | 291 |

It is recognized from the measured plasmin activities that the domain of the fibrinogen molecule which is responsible for the stimulation and for the oxidation intensified stimulation is the D region.

EXAMPLE 6

Amino acid analysis of oxidized and unoxidized FDP-D 1 mg/ml of fibrinogen degradation product D (peak 1, purified in accordance with Example 5) was incubated in accordance with Example 1 in 50 mmol/l Tris buffer, pH 8.5, with and without the addition of 5 mmol/l chloramine T for 30 min at 37° C. This was followed by dialysis against 100 times the volume of distilled water for 48 h at 4° C. and the use of 1.2 nM protein per analysis in a LKB 4150 amino acid analyzer under varied standard hydrolysis conditions (24 h, 110° C. in vacuo, 3N p-toluenesulfonic acid). The results are mean values of triple determinations. The amino acid tryptophan could not be determined under the conditions used (Table 7).

TABLE 7

| Amino acid composition | D (%) | oxid. D (%) |
|---|---|---|
| Asp | 13.2 | 12.5 |
| Thr | 4.0 | 4.3 |
| Ser | 5.8 | 6.1 |
| Glu | 10.3 | 12.4 |
| Pro | 4.9 | 5.6 |
| Gly | 11.6 | 12.2 |
| Ala | 4.7 | 4.5 |
| Cys | 0.4 | 0.4 |
| Val | 3.9 | 4.4 |
| Met | 0.8 | <0.1 |
| Ile | 3.3 | 3.5 |
| Leu | 5.3 | 5.6 |
| Tyr | 2.8 | 2.4 |
| Phe | 3.1 | 3.0 |
| His | 3.2 | 3.3 |
| Lys | 8.4 | 8.2 |
| Arg | 6.3 | 6.9 |

The two proteins differ essentially in the lack of methionine in oxidized D. Methionine sulfoxide migrates in the analyzer to another site and is not indicated as methionine.

EXAMPLE 7

Increased affinity for fibrin thrombi of oxidized FDP compared with unoxidized FDP: detection of thrombi 0.5 ml of plasma was clotted by adding 50 μl of 0.2 mol/l CaCl$_2$ and 0.5 IU of thrombin. The resulting clots were then washed by centrifuging three times in 20 times the amount of phosphate buffered saline (PBS) and incubated for one hour at room temperature in, in each case, a PBS solution of 0.5 ml of oxizided FDP (FDP=plasmin degradation of fibrinogen in the presence of 5 mmol/l EDTA) (1 mg/ml) and 0.5 ml of unoxidized FDP (1 mg/ml) or, respectively, 0.5 ml of fibrinogen (1 mg/ml) (control=FDP solutions without clots). Subsequently the residual stimulation power of the FDP in the supernatant liquor was tested by incubating 50 μl of a tissue plasminogen activator solution (500 IU tc-t-PA/ml) in PBS with 100 μl of supernatant liquor, 200 μl of plasminogen (=1 CTA-U in 100 mmol/l Tris, 100 mmol/l NaCl, 1% (w/v) $^R$Haemaccel, 0.1% (w/v) $^R$Triton X 100, pH 8.4) and 100 μl of 3 mmol/l D-norvalyl-cyclohexyl-alanyl-lysyl-paranitroanilide (HD-Nva-CHA-Lys-pNA) in distilled water for 8 min at 37° C., stopping with 500 μl of 8.5 mol/l acetic acid and determining the extinction at 405 nm.

See Table 8 for result.

TABLE 8

| Sample = stimulus (1–3) | Plasmin activity (t-PA) A$_{405\,nm}$/8 min (mU) | t-PA stimulation power* |
|---|---|---|
| Without clots: | | |
| 1 oxid. FDP | 1,235 ± 14 | 15.4 |
| 2 unoxid. FDP | 587 ± 6 | 7.3 |
| 3 Fibrinogen | 216 ± 1 | 2.7 |
| With clots: | | |
| 1 oxid. FDP | 755 ± 4 | 61%** |
| 2 unoxid. FDP | 465 ± 1 | 80% |
| 3 Fibrinogen | 171 ± 2 | 80% |
| Control (stimulus) percentage | 80 ± 3 | |

*Ratio of t-PA activity with stimulus: t-PA activity without stimulus
**in % without clots It can be seen that the greatest decrease in the t-PA stimulation power of the supernatant liquor occurs with oxidized FDP, which means that oxidized FDP has a higher binding affinity to fibrin than unoxidized FDP or fibrinogen.

EXAMPLE 8

Oxidation of fibrin monomers leads to an intensification of their stimulation properties towards t-PA 100 μl (1 mg/ml) of fibrin monomers in buffer were incubated with chloramine T of different concentrations for 10 min at 37° C. The oxidation was then terminated by adding 100 μl of mmol/l N-acetyl-methionine, pH 8.4, and 200 μl of tc-t-PA (=10 IU) in buffer, 200 μl of plasminogen (1 CTA-U) in buffer and 100 μl of 3 mmol/l HD-Nva-CHA-Lys-pNA in distilled water were added and the mixtures incubated for 24 min at 37° C.

The substrate conversion was terminated by adding 500 μl of 8.5 mol/l acetic acid and the resulting extinction at 405 nm was determined.

TABLE 9

Result:

| Chloramine T addition (50 μl) (mmol/l) | Plasmin activity (mA) fibrin monomers | buffer |
|---|---|---|
| 0 | 1274 ± 5 | 244 ± 3 |
| 1 | 551 ± 5 | |
| 5 | 795 ± 11 | |
| 10 | 2095 ± 45 | |
| 20 | 2287 ± 4 | |
| 40 | 2276 ± 4 | 248 ± 8 |

It can be seen that increasing concentrations of chloramine after an initial decrease subsequently leads to an increase in the t-PA stimulation. Addition of methionine does not impair the measurement method, as can be shown in the buffer control.

I claim:

1. A derivative of fibrin, fibrin degradation products or fibrinogen degradation products, or partial sequences thereof, comprising the D-region of fibrinogen, wherein methionine residues in the basic amino acid sequence have been converted to methionine sulfoxide using an oxidant under conditions in which the oxidant is specific for methionine, and wherein essentially no tyrosine residues are iodized.

2. A medicament comprising a derivative as claimed in claim 1 and, optionally, pharmaceutically acceptable adjuvants and excipients.

3. A process for the preparation of a derivative of fibrin, fibrin degradation products or fibrinogen degradation products, or partial sequences thereof, comprising the D-region of fibrinogen, which comprises converting methionine residues in the basic amino acid sequence to methionine sulfoxide using an oxidant under conditions in which the oxidant is specific for methionine and in which essentially no tyrosine residues are iodized.

4. The process as claimed in claim 3, wherein the methionine-specific oxidant is a chloramine.

5. The process as claimed in claim 3, wherein degradation products are used which have been prepared in the presence of chelate-forming agents.

6. The process as claimed in claim 3, wherein the oxidation is a carried out at pH 7-9.5.

* * * * *